United States Patent [19]
Davis et al.

[11] Patent Number: 5,848,693
[45] Date of Patent: Dec. 15, 1998

[54] LAPAROSCOPIC SURGICAL TRAY WITH APERTURED CLIPS

[76] Inventors: Steven J. Davis, 300 Sheridan Rd., Waterloo, Iowa 50701; Janine Reuter, 725 Hall Ave., Waterloo, Iowa 50703; Daniel M. Johnson, 233 Byrnes Dr., Waterloo, Iowa 50701

[21] Appl. No.: 964,247

[22] Filed: Nov. 4, 1997

[51] Int. Cl.⁶ .............................. B65D 1/36; A61B 19/00
[52] U.S. Cl. ........................... 206/370; 128/849; 206/438
[58] Field of Search .................................. 206/363, 369, 206/366, 370, 562–569, 438; 128/849, 846; 422/297, 300, 310

[56] References Cited

U.S. PATENT DOCUMENTS

| | | | |
|---|---|---|---|
| 3,133,635 | 5/1964 | Gordon et al. ........................... | 206/366 |
| 3,483,494 | 12/1969 | Cromie . | |
| 4,068,655 | 1/1978 | LeRoy . | |
| 4,466,430 | 8/1984 | Shultz . | |
| 4,626,971 | 12/1986 | Schultz ............................... | 206/370 X |
| 4,793,483 | 12/1988 | Holmes .................................. | 206/363 |
| 5,005,590 | 4/1991 | Eldridte, Jr. et al. . | |
| 5,036,866 | 8/1991 | Eldridge, Jr. et al. . | |
| 5,170,804 | 12/1992 | Glassman .............................. | 128/849 |
| 5,173,273 | 12/1992 | Brewer ................................. | 206/562 |
| 5,195,538 | 3/1993 | Eldridge, Jr. et al. . | |
| 5,339,955 | 8/1994 | Horan et al. ........................... | 206/370 |

FOREIGN PATENT DOCUMENTS

| | | |
|---|---|---|
| 1 197 745 | 12/1985 | Canada . |
| PCT 0043840 | 8/1981 | European Pat. Off. . |

*Primary Examiner*—Bryon P. Gehman
*Attorney, Agent, or Firm*—Zarley, McKee, Thomte, Voorhees & Sease

[57] ABSTRACT

A surgical tray retains surgical instruments adjacent an operating area or surgical field. The surgical tray comprises a base portion, and outer wall, a compartment for retaining surgical instruments defined by the base portion and at least a portion of the outer wall, and a plurality of clips spaced apart along the outer surface of the outer wall for securing the surgical tray to a surgical drape adjacent the operating area. The compartment includes a plurality of dividing walls having grooves for separating and retaining surgical instruments to enable members of an operating team to quickly and easily grasp surgical instruments in the surgical tray.

10 Claims, 3 Drawing Sheets

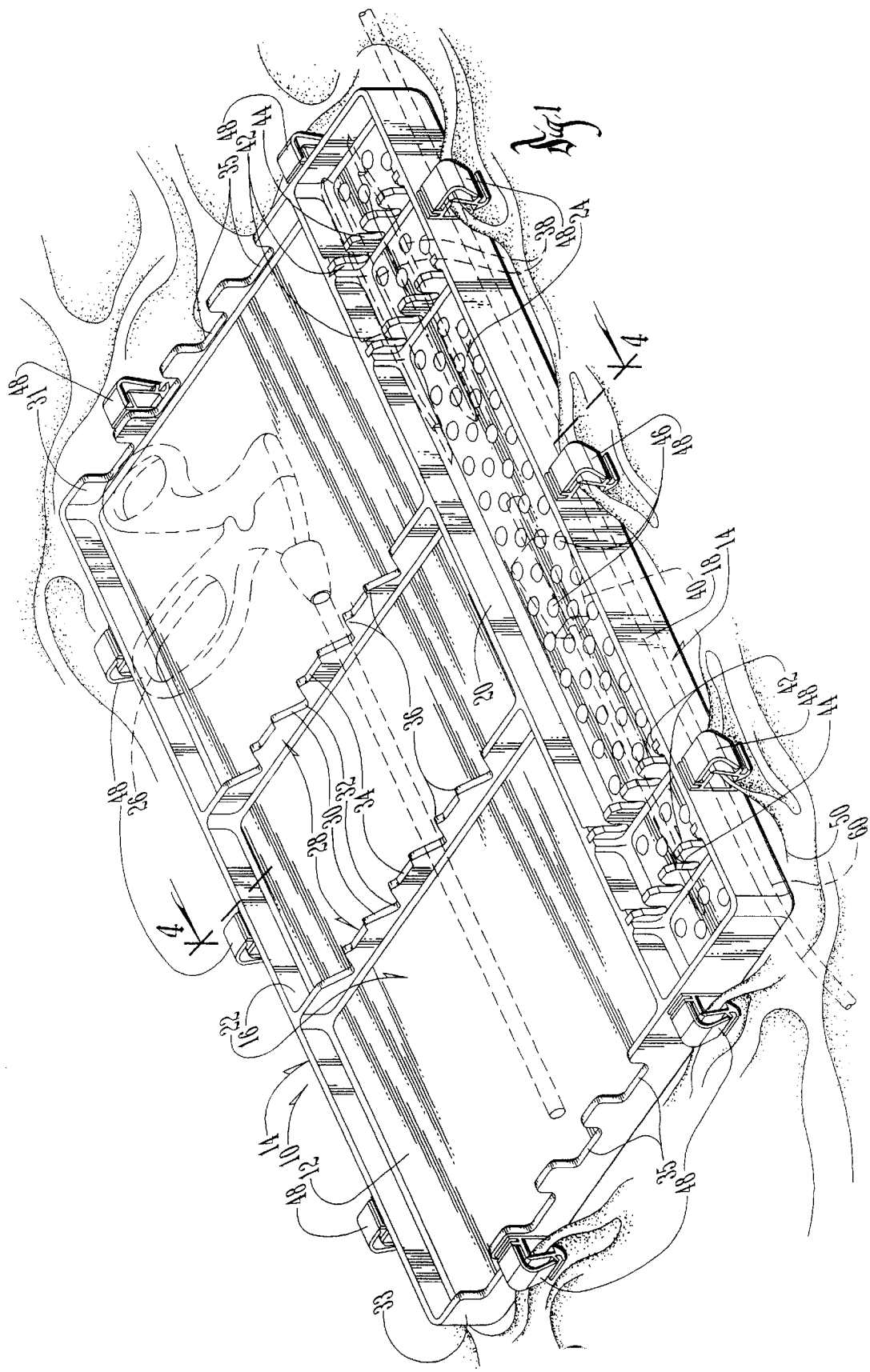

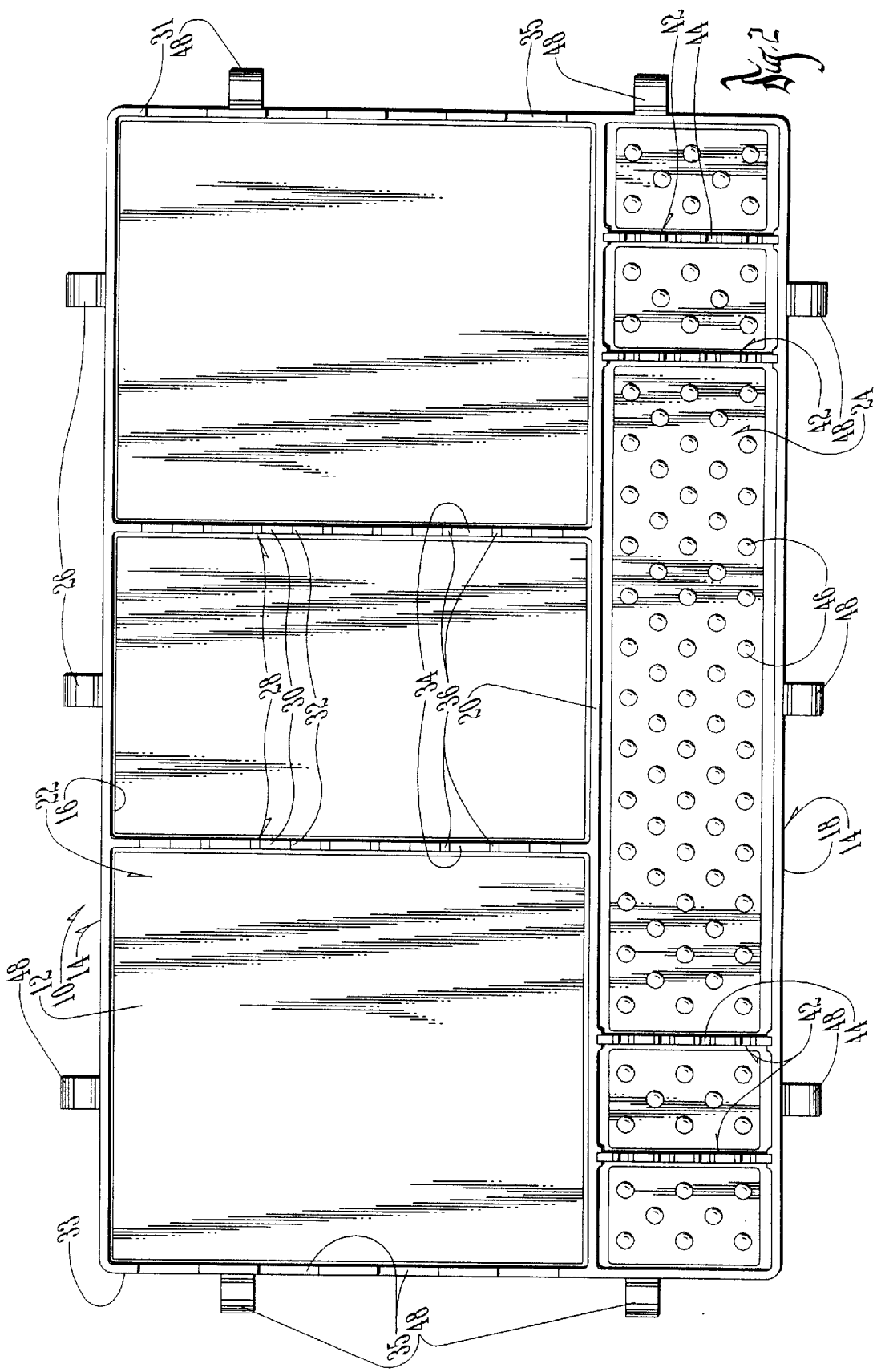

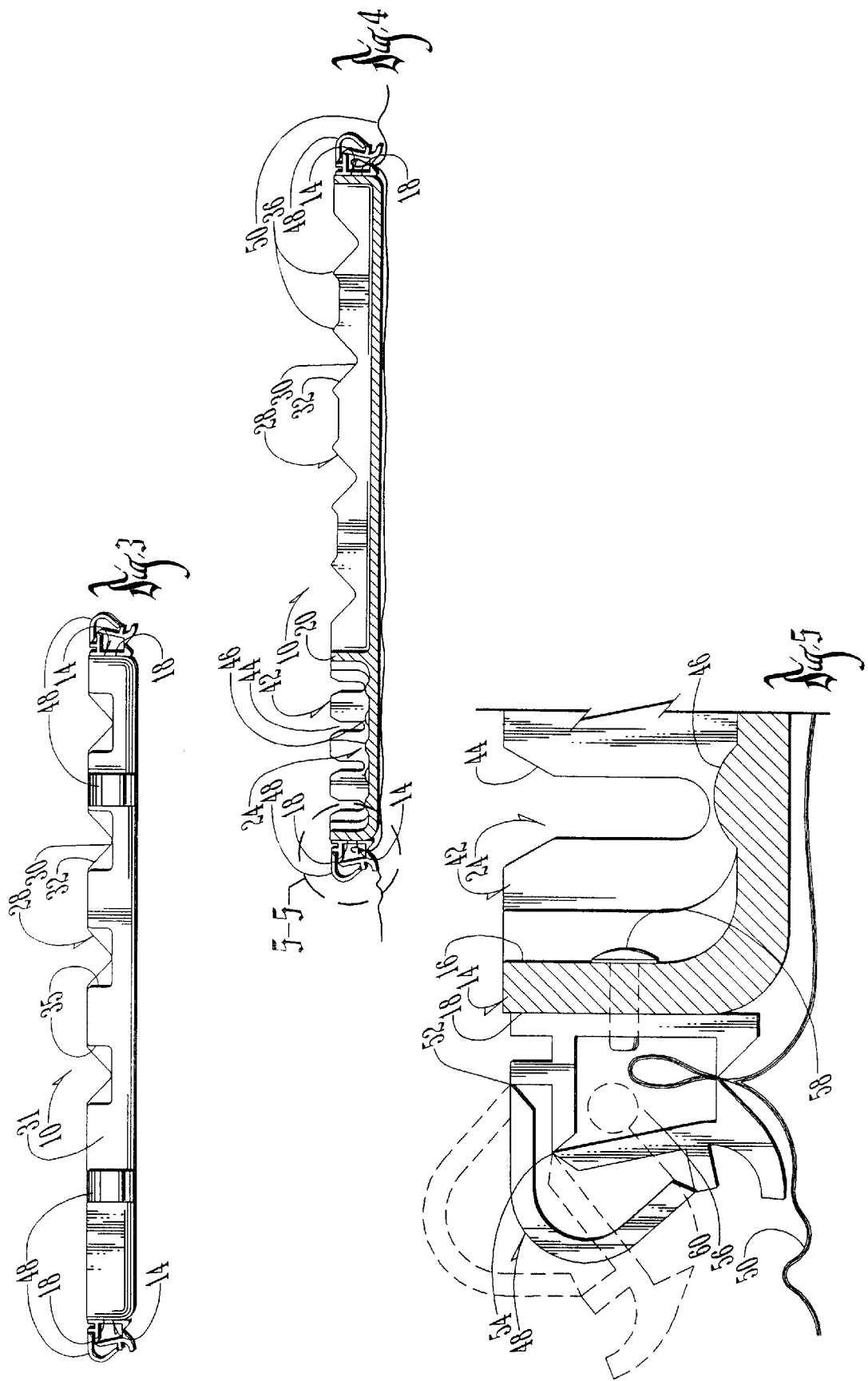

LAPAROSCOPIC SURGICAL TRAY WITH APERTURED CLIPS

BACKGROUND OF THE INVENTION

The present invention relates generally to the field of devices for retaining surgical instruments, and more particularly, to a surgical tray which may cooperate with a surgical drape to retain medical instruments during surgery.

In the course of surgery, a wide variety of instruments are used. Laparoscopic surgical procedures, in particular, specifically require several instruments, some which have a singular use in a specific order and others which have multiple, alternating usages. Although the surgeon may use only one or two instruments at a time, the remaining instruments must be readily available for immediate use.

Sterile surgical drapes are laid on the patient near the operating area for sterile technique. Instruments not used as often may be laid across the draped patient whenever convenient. Although simple, this procedure does not insure a secure, defined location for the instruments. Surgical instruments may slip or fall from the sterile field or become entangled with other instruments. This results in confusion and frustration among the members of the operating team, as instruments must be rapidly exchanged as needed. Furthermore, the lack of a secure location for sharp instruments, such as needles, scalpels, and trocars, significantly increases the risk of injury to members of the operating team. Thus, there is a need for a device that effectively retains surgical instruments in defined locations so that instruments may be exchanged rapidly as needed, reduces the risk of injury to the operating team, and assures a sterile environment for the instruments during the surgical procedure.

Several attempts have been made to provide such a device. These surgical trays have usually suffered, however, from one or more shortcomings, including failure to provide predefined locations for the surgical instruments, and ineffective means and methods to secure the surgical tray to a surgical drape.

Accordingly, a primary objective of the present invention is the provision of an improved surgical tray for retaining surgical instruments near the operating surgeon.

A further objective of the present invention is the provision of a surgical tray that effectively secures to a surgical drape near the operating area.

Another objective of the present invention is the provision of a surgical tray that includes predefined locations to store surgical instruments.

Another objective of the present invention is the provision of a surgical tray that allows for easy storage and removal of the surgical instruments next to the operating area.

A still further objective of the present invention is an improved method for using a surgical tray during surgery.

Another objective of the present invention is the provision of a surgical tray that is efficient in operation, economical to manufacture, and durable in use.

These and other features, objectives, and advantages will become apparent to those skilled in the art with reference to the accompanying specification.

SUMMARY OF THE INVENTION

The present invention is a surgical tray for retaining surgical instruments adjacent an operating area or surgical field. The tray comprises a base portion, an outer wall, one or more compartments for retaining the surgical instruments defined by the base portion and at least a portion of the outer wall, and a plurality of clips spaced apart along the outer wall for securing the surgical tray to a surgical drape adjacent the surgical field. In their preferred form, the clips have an aperture for receiving tubing and surgical instrument cords.

Optionally, the first compartment includes a plurality of dividing walls, each having a plurality of grooves for separating and retaining surgical instruments. The grooves in adjacent dividing walls are aligned and disposed such that the surgical instruments are raised above the base portion of the tray. This enables members of the operating team to quickly and easily grasp surgical instruments in the tray. The surgical tray may also include end walls having notches that are aligned with the grooves of the dividing walls so that larger instruments may be accommodated as they protrude beyond the end walls of the tray.

One of the unique features of the invention is that the surgical try may be designed such that it is substantially symmetrical about a mid-point between opposing end walls. This unique features allows doctors and other members of the operating team to use and access surgical instruments in the tray from either side of the patient.

The invention also includes a method for using a surgical tray to retain surgical instruments during surgery, including the steps of providing a surgical tray as described above, placing a surgical drape over the patient, positioning the surgical tray on the surgical drape, and attaching the clips of the surgical tray to the surgical drape. Tubing and surgical instrument cords may also be inserted through apertures in the clips.

BRIEF DESCRIPTION OF THE DRAWINGS

FIG. 1 is a perspective view of the surgical tray of the present invention.

FIG. 2 is a top elevational view of the surgical tray of FIG. 1.

FIG. 3 is an end elevational view of the surgical tray of FIG. 1.

FIG. 4 is a sectional view along line 4—4 of FIG. 1.

FIG. 5 is an enlarged sectional view of area 5—5 of FIG. 4, showing the clip in an open and closed position.

DETAILED DESCRIPTION OF THE PREFERRED EMBODIMENT

FIG. 1 shows a surgical tray 10 formed from a base portion 12 and an outer wall 14. The outer wall 14 has both an inner surface 16 and an outer surface 18. A common wall 20 divides the surgical tray 10 into a first compartment 22 and a second compartment 24, both rectangular in shape.

The first compartment 22 is defined by the base portion 12, a portion of the outer wall 14, and the common wall 20. As shown in FIG. 1, the first compartment 22 is suitable for retaining and securing elongated laparoscopic surgical instruments 26 having large handles. The outer wall 14 and common wall 20 are radiused with the base portion 12 so that there are no 90° angles at their junctures.

Dividing walls 28 project upward from the base portion between the outer wall 14 and the common wall 20. The dividing walls 28 are spaced apart and contains a series of V-shape grooves 30. The grooves 30 of the dividing walls 28 are aligned to facilitate defining fixed locations for the placement of long cylindrical surgical instruments 26. Note that the base 32 of each groove 30 is disposed above the base portion 12 to maintain a spaced-apart relationship between the surgical instrument 26 and the base portion 12. This facilitates easier pick-up and handling of the surgical instruments 26.

The opposing end walls 31 and 33 include notches 35. substantially aligned with the grooves 30 in the dividing walls 28 to allow longer surgical instruments to protrude beyond both end walls 31 and 33 of the surgical tray 10. The notches 35 also provide resistance against sliding when the base portion 12 is angled.

The dividing walls 28 also include a series of raised flats 34 disposed between the grooves 30. These raised flats 34 are used to support larger, more balbous instruments. Posts 36 on both ends of the flats 34 prevent the larger instruments on the flats 34 from sliding.

The second compartment 24 of the surgical tray 10 is rectangular in shape and is defined by a segment of the base portion 12, a portion of the outer wall 14, and the common wall 20. The second compartment is intended to provide space for instruments such as trochars 38 and various needles 40. The second compartment includes a plurality of partitions 42. Each of the partitions 42 includes a series of slots 44 that aid in retaining the scalpels and other sharp instruments. In their preferred form, the partitions 42 are removable to allow the second compartment to be customized for a particular application.

The segment of the base portion 12 defining the second compartment 24 has a plurality of raised areas or bumps 46. This texturizing of the base portion 12 aids the members of the surgery team in grasping the surgical instruments.

The surgical tray 10 is substantially symmetrical about a mid-point between end walls 31 and 33. This feature of the invention allows members of the surgery team to work from either side of the patient, as the surgical instruments (26, 38, 40) may be stored in opposing directions.

A plurality of clips 48 are disposed along the outside surface 18 of the outer wall 14. The clips 48 are used to fasten and secure the surgical tray 10 to a surgical drape 50. The preferred clip 48 may be purchased commercially from Wells-Lamont. FIG. 5 shows the clip 48 in both an open and closed position. The clip 48 is naturally hinged about points 52 and 54. This over-center, snap action design allows the clip 48 to remain open while positioning the surgical tray 10. The open area or aperture 56 of the clip in the closed position provides a positive routing location for tubing and surgical instrument cords 60. The clips 48 are preferably riveted to the outside surface 18 of the outer wall 14 using a rivet 58 to allow rotational adjustment.

In its preferred form, the base portion 12, outer wall 14, dividing walls 28, and common wall 20 are integrally formed. It is also preferred that the entire surgical tray 10 be made from a radio lucent material. Using a radio lucent material gives the surgical tray 10 the advantage of having no metallic parts to interfere with X-rays. Whatever material is used to form the surgical tray 10 may also be recyclable and re-sterilizable. In its preferred form, the first compartment 22 is 8"×19", and the second compartment 24 is 3"×19".

Preferably, the tray 10 is rectangular as shown in the drawings. The dividing walls 28 and partitions extend transversely and the common wall 20 extends longitudinally. Thus, the first compartment 22 and second compartment 24 are elongated so as to hold long or short instruments.

The surgical tray 10 as described above provides an efficient and facile method for retaining surgical instruments during surgery. The method includes placing the surgical drape 50 over the patient, positioning the surgical tray 10 on the surgical drape 50 proximate the operating area. Finally, the surgical tray 10 is attached to the surgical drape 50 using the clips 48. The clips 48 also allow repositioning of the tray 10 if necessary. Tubing and instrument cords 60 can also be inserted into the aperture 56 of the clips 48 either before or after the clips are closed.

Whereas the invention has been shown and described in connection with the preferred embodiments thereof, it will be understood that many modifications, substitutions, and additions may be made which are within the intended broad scope of the following claims. From the foregoing, it can be seen that the present invention accomplishes at least all of the stated objectives.

What is claimed is:

1. A tray for retaining surgical instruments and for use with a surgical drape, comprising:

a base portion having a periphery;

an outer wall projecting upwardly from the periphery, the outer wall having an inner surface and an outer surface;

a first compartment defined by the base portion and at least a portion of the outer wall;

a plurality of clips mounted on the outer surface of the outer wall for securing the tray to the surgical drape; and the clips each having an aperture adapted for receiving tubing and surgical instrument cords.

2. The tray of claim 1 further comprising a first dividing wall projecting from the base portion within the first compartment and having a plurality of grooves for separating and retaining the surgical instruments.

3. The tray of claim 2 wherein the dividing wall is removable.

4. The tray of claim 2 further comprising a second dividing wall projecting from the base portion within the first compartment and spaced-apart from the first dividing wall, the second dividing wall having a plurality of grooves aligned with the grooves of the first compartment for separating and retaining the surgical instruments.

5. The tray of claim 4 wherein the grooves of the first and second dividing walls are disposed above said base portion for maintaining a spaced-apart relationship between the surgical instruments and the base portion.

6. The tray of claim 4 wherein the outer wall includes opposite first and second end walls each having notches aligned with the grooves of the first and second dividing walls to accommodate a protrusion of the surgical instruments.

7. The tray of claim 1 wherein the outer wall includes a first end wall and a second end wall opposite the first end wall, each of the first and second end walls having notches to accommodate a protrusion of the surgical instruments.

8. The tray of claim 1 wherein the tray is integrally formed of a radio lucent material.

9. The tray of 1 wherein the base portion is textured to aid in grasping the surgical instruments.

10. A method of using a surgical tray for retaining surgical instruments during surgery on a patient, comprising:

placing a surgical drape over the patient;

positioning the surgical tray on the surgical drape, the tray having a plurality of clips secured thereto, each clip having an aperture;

attaching the clips to the surgical drape to secure the surgical tray to the surgical drape; and inserting at least one tubing and surgical instrument cords through the apertures in the clips.

* * * * *